US00PP23836P2

(12) United States Plant Patent
Meilland

(10) Patent No.: US PP23,836 P2
(45) Date of Patent: Aug. 20, 2013

(54) SHRUB ROSE PLANT NAMED 'MEIPINAPIO'

(50) Latin Name: *Rosa hybrida*
Varietal Denomination: Meipinapio

(75) Inventor: Alain A. Meilland, Antibes (FR)

(73) Assignee: Meilland International S.A., Le Luc (FR)

( * ) Notice: Subject to any disclaimer, the term of this patent is extended or adjusted under 35 U.S.C. 154(b) by 69 days.

(21) Appl. No.: 13/385,125

(22) Filed: Feb. 3, 2012

(51) Int. Cl.
*A01H 5/00* (2006.01)

(52) U.S. Cl.
USPC ..... Plt./107

(58) Field of Classification Search
USPC ..... Plt./107
See application file for complete search history.

*Primary Examiner* — Annette Para
(74) *Attorney, Agent, or Firm* — Buchanan Ingersoll & Rooney PC

(57) ABSTRACT

A new and distinct variety of landscape shrub rose plant is provided which abundantly forms in clusters on a nearly continuous basis attractive small ochre-pink blossoms. The plant exhibits a low, compact and bushy growth habit. Good disease tolerance including resistance to Black Spot has been observed. The attractive dark green foliage contrasts nicely with the blossom coloration. The new variety is particularly well suited for growing as attractive ornamentation in the landscape.

1 Drawing Sheet

Figures 1, 2, 3, 4, 5, 6, 7, 8, 9, 10, 11, 12, 13, 14, 15, 16, 17, 18, 19:
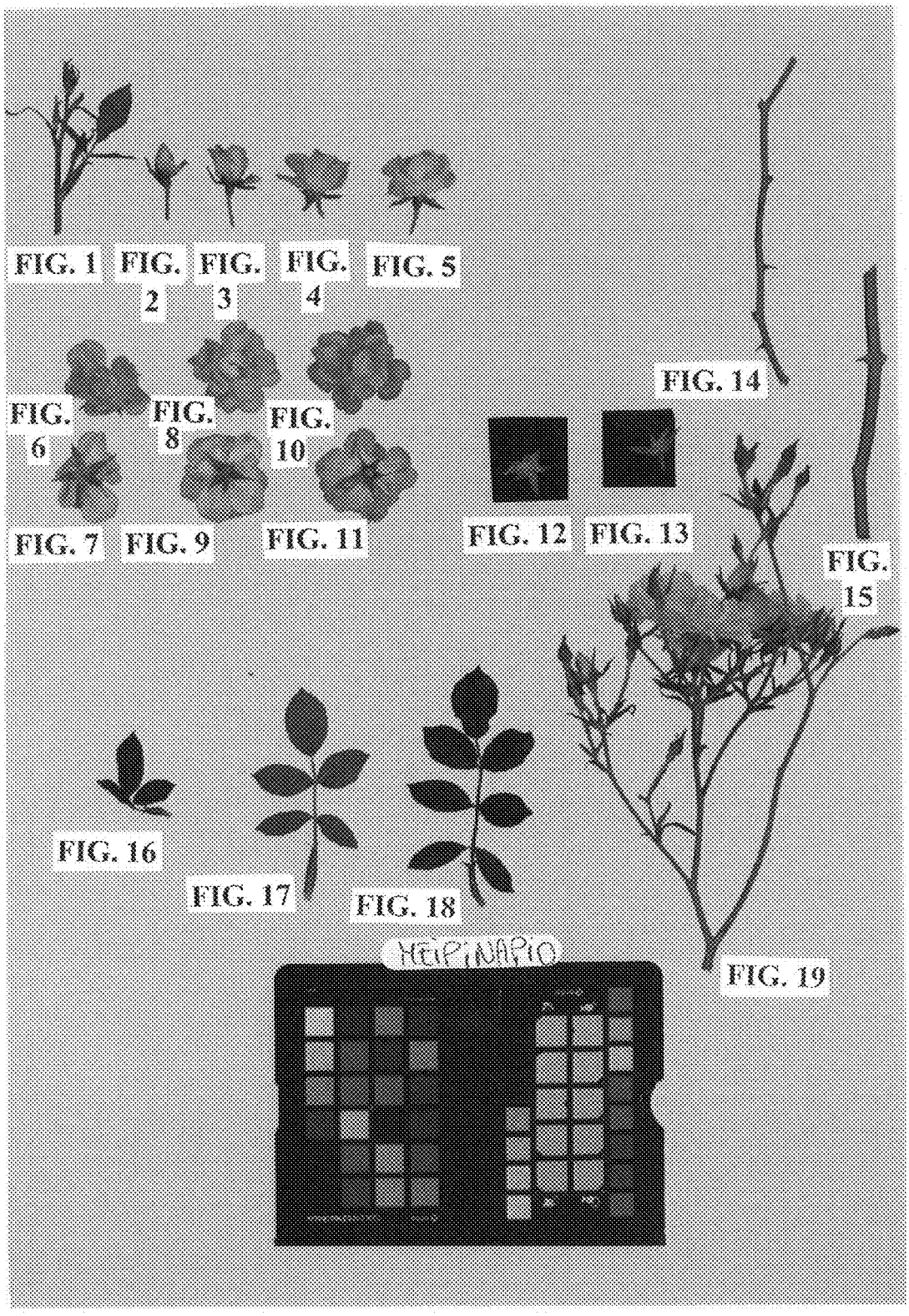

Botanical/commercial classification: *Rosa hybrida*/Shrub Rose.

Varietal denomination: cv. Meipinapio.

SUMMARY OF THE INVENTION

The new variety of *Rosa hybrida* landscape shrub rose plant is provided. The new variety is believed to be a spontaneous mutation of unknown causation of the 'Meigalpio' variety (U.S. Plant Pat. No. 17,877, granted Jul. 24, 2007). A single plant of the new variety was discovered while growing in a nursery setting at Le Cannet des Maures, Var, France, among a block of plants of the 'Meigalpio' variety. The plant was found to display a distinctive dissimilar blossom coloration and was thereafter carefully studied. Had this plant not been discovered and thereafter preserved it would have been lost to mankind.

It was found that the new variety of the present invention (a) exhibits a low, compact and bushy growth habit,
(b) abundantly forms in clusters on a nearly continuous basis attractive small light ocher-pink blossoms unlike the brilliant red-pink blossoms of the 'Meigalpio' variety (U.S. Plant Pat. No. 17,877),
(c) forms dense dark green foliage having a glossy aspect that contrasts well with the blossom coloration, and
(d) is particularly well suited for growing as attractive ornamentation in the landscape.

The tolerance to diseases is good. During observations to date the plant has been found to be particularly resistant to Black Spot.

The new variety well meets the needs of the horticultural industry and can be grown to advantage in parks and gardens where attractive ornamentation is desired.

The new variety readily can be distinguished from its parent 'Meigalpio' variety in view of its distinctive light ocher-pink blossoms.

The new variety also can be readily distinguished from ancestors of 'The Fairy' variety (non-patented in the United States), the 'Kormax' variety (non-patented in the United States), and the 'Morpapplay' variety (U.S. Plant Pat. No. 6,548). 'The Fairy' variety forms dissimilar light pink blossoms, the 'Kormax' variety forms larger red blossoms having only six petals, and the 'Morpapplay' variety forms dark orange-red blossoms having a bright yellow eye.

The new variety has been found to undergo asexual propagation in France by a number of routes, including budding, grafting, and the use of cuttings. Asexual propagation by the above-mentioned techniques in France has shown that the characteristics of the new variety are stable and are strictly transmissible by such asexual propagation from one generation to another. Accordingly, the new variety can be asexually reproduced in a true-to-type manner.

The new variety has been named 'Meipinapio'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately eighteen months of age and were observed during October while reproduced by the use of cuttings and growing outdoors at Le Cannet des Maures, Var, France. Standard colors are presented at the bottom for comparative purposes.

FIG. 1—illustrates a specimen of a young shoot;

FIG. 2—illustrates a specimen of a floral bud at the opening of the sepals;

FIG. 3—illustrates a specimen of a floral bud at the further opening of the sepals;

FIG. 4—illustrates a specimen of a floral bud at the opening of the petals;

FIG. 5—illustrates a specimen of a flower in the course of opening;

FIG. 6—illustrates a specimen of an opening flower—plan view—obverse;

FIG. 7—illustrates a specimen of an opening flower with sepals—plan view—reverse;

FIG. 8—illustrates a specimen of an open flower—plan view—obverse;

FIG. 9—illustrates a specimen of an open flower with sepals—plan view—reverse;

FIG. 10—illustrates a fully open flower—plan view—obverse;

FIG. 11—illustrates a fully open flower with sepals—plan view—reverse;

FIG. 12—illustrates a specimen of a floral receptacle showing the arrangement of the stamens and pistils;

FIG. 13—illustrates a specimen of a floral receptacle showing the arrangement of the pistils (stamens removed);

FIG. 14—illustrates a specimen of a flowering stem;

FIG. 15—illustrates a specimen of a main branch;

FIG. 16—illustrates a specimen of a leaf with three leaflets—plan view—upper surface;

FIG. 17—illustrates a specimen of a leaf with five leaflets—plan view—under surface;

FIG. 18—illustrates a specimen of a leaf with seven leaflets—plan view—upper surface; and FIG. 19—illustrates a cluster of buds.

DETAILED DESCRIPTION

The chart used in the identification of the colors is that of The Royal Horticultural Society (R.H.S. Colour Chart—1995 or equivalent). The description is based on the observation of eighteen month-old plants during October while growing on the plant's own roots outdoors at Le Gannet des Maures, Var, France.

Class: Landscape Shrub.

Plant:

*Height*.—Approximately 30 to 40 cm on average at the end of the growing season.

*Width*.—Approximately 30 to 40 cm on average at the end of the growing season.

*Habit*.—Low, bushy and compact.

Branches:

*Color*.—Young stems: near Yellow-Green Group 144A. adult wood: near Yellow-Green Group 146B.

*Thorns*.—Size and quantity: on 10 cm of young stems approximately 2 on average approximately 0.6 cm in length; and on 10 cm of adult stems approximately 6 on average approximately 0.6 cm in length. color: near Red Group 49D with Yellow Group 11D at the tip on young stems, and near Greyed-Orange Group 166A and 166B on adult stems. configuration: elongated on the upper surface and concave on the under surface with an ovate base.

*Smaller prickles*.—Commonly absent.

Leaves:

*Stipules*.—Adnate, pectinate, and rather broad, smooth, approximately 2.3 cm in length on average, approximately 0.7 cm in width on average, near Yellow-Green Group 146A on the upper surface, and near Yellow-Green Group 146B on the under surface.

*Petioles*.—Upper surface: near Yellow-Green Group 146A in coloration. under surface: near Yellow-Green Group 146A and 146B in coloration. length: approximately 3.7 cm for the terminal leaflet.

*Petiole rachis*.—Upper surface: near Yellow-Green Group 146A in coloration. under surface: near Yellow-Green Group 146B in coloration.

*Leaflets*.—Number: 3, 5 and 7 (most often). shape: generally elliptical with a cuneiform base and an acuminate tip. size: the terminal leaflets commonly are approximately 2.6 cm in length on average, and approximately 1.2 cm in width on average. serration: single and fine. texture: firm and consistent. general appearance: rather dense, dark green with a glossy aspect. color (young foliage): upper surface: near Green Group 137A. under surface: near Yellow-Green Group 146B. color (adult foliage): upper surface: near Green Group 139A. under surface: near Yellow-Green Group 146B.

Inflorescence:

*Number of flowers*.—Commonly approximately 5 to 15 flowers per stem in a cluster.

*Peduncle*.—Near Yellow-Green Group 144A in coloration, smooth, approximately 2 to 3 cm in length on average, and approximately 0.2 cm in diameter on average.

*Sepals*.—Upper surface: tomentose and near Yellow-Green Group 147D in coloration. under surface: smooth and near Yellow-Green Group 144A in coloration. configuration: narrow with a longish point and rounded at the base. size: approximately 1.2 cm in length on average, and approximately 0.4 cm in width at the widest point on average. margins: two sepals commonly possess no extensions and three sepals commonly possess very weak extensions.

*Buds*.—Shape: conical. size: small. length: approximately 1.2 cm on average. width: approximately 1 cm at the widest point on average. color: upper surface: near Red Group 56A and 56B suffused with near Red-Purple Group 68B as the calyx breaks. under surface: near Yellow Group 13C and 13D amply suffused with Red Group 56C and more or less margined with Red-Purple Group 68A and 68B. basal petal spot: near Yellow Group 13C on both surfaces.

*Flower*.—Shape: generally cup-shaped. diameter: approximately 4 cm on average. color (in course of opening): upper surface: near Red Group 56A and 56B suffused with Red-Purple Group 68B. under surface: near Yellow Group 13C and 13D amply suffused with near Red Group 56C and more or less margined with Red-Purple Group 68A and 68B. basal petal spot: near Yellow Group 13C on both surfaces. color (open flower): upper surface: near Red Group 56A and 56B suffused with red-Purple Group 68B. under surface: near Yellow Group 13C and 13D amply suffused with near Red Group 56C and more or less margined with Red-Purple Group 68A and 68B. basal petal spot: near Yellow Group 13C on both surfaces. fragrance: none. lasting quality: the blossoms commonly last approximately 13 to 15 days on the plant on average depending upon the environment conditions, and have not been evaluated when present in a vase since the new variety is primarily intended to provide ornamentation in the garden. petal number: approximately 15 to 17 on average under normal growing conditions. petal size: approximately 2 cm in length on average, and approximately 1.6 cm in width on average. petal texture: generally firm and consistent. petaloids: commonly absent. petal shape: generally possess a flattened tip and a cuneiform base. petal arrangement: imbricated. petal drop: very good with the petals commonly detaching cleanly before drying.

stamen number: approximately 39 on average. anthers: regularly arranged around the styles, approximately 0.1 cm in size on average, and near Yellow-Orange Group 22D in coloration. filaments: near Yellow Group 11D in coloration, and approximately 0.3 cm in length on average. pistils: approximately 15 on average. stigmas: near Greyed-Yellow Group 160B in coloration, and approximately 0.1 cm in size. styles: near Greyed-Green Group 191C in coloration, and approximately 0.3 cm in length on average. receptacle: smooth, near Yellow-Green Group 144A in coloration, and pitcher-shaped in longitudinal section. The length commonly is approximately 0.5 cm on average and the width commonly is approximately 0.3 cm on average. hips: none observed during observations to date.

Development:

*Vegetation*.—Strong.

*Blooming*.—Early season, abundant and nearly continuous.

*Resistance to diseases*.—Good disease tolerance particularly with respect to Black Spot during observations to date.

*Aptitude to bear fruit*.—None observed during observations to date.

I claim:

1. A new and distinct landscape shrub rose plant characterized by the following combination of characteristics:

(a) exhibits a low, compact and bushy growth habit, (b) abundantly forms in clusters on a nearly continuous basis attractive small light ocher-pink blossoms unlike the brilliant red-pink blossoms of the 'Meigalpio' variety (U.S. Plant Pat. No. 17,877), (c) forms dense dark green foliage having a glossy aspect that contrasts well with the blossom coloration, and (d) is particularly well suited for growing as attractive ornamentation in the landscape;

substantially as herein shown and described.

* * * * *

YEUPINARIO